United States Patent
Beck (10) Patent No.: US 9,429,564 B2
(45) Date of Patent: Aug. 30, 2016

(54) SYSTEM AND METHOD FOR ELUTING AND TESTING SUBSTANCE FROM EXHALED AEROSOL SAMPLE

(71) Applicant: Sensa Bues AB, Sollentuna (SE)

(72) Inventor: Olof Beck, Salts-jo-Boo (SE)

(73) Assignee: Sensa Bues AB, Sollentuna (SE)

( * ) Notice: Subject to any disclaimer, the term of this patent is extended or adjusted under 35 U.S.C. 154(b) by 0 days.

(21) Appl. No.: 14/427,229

(22) PCT Filed: Sep. 11, 2013

(86) PCT No.: PCT/EP2013/068860
§ 371 (c)(1),
(2) Date: Mar. 10, 2015

(87) PCT Pub. No.: WO2014/041045
PCT Pub. Date: Mar. 20, 2014

(65) Prior Publication Data
US 2015/0226726 A1    Aug. 13, 2015

Related U.S. Application Data

(60) Provisional application No. 61/699,307, filed on Sep. 11, 2012.

(30) Foreign Application Priority Data

Sep. 11, 2012  (EP) .................................... 12183840

(51) Int. Cl.
*G01N 33/48* (2006.01)
*G01N 33/497* (2006.01)
(Continued)

(52) U.S. Cl.
CPC .............. *G01N 33/497* (2013.01); *A61B 5/082* (2013.01); *A61B 5/097* (2013.01); *A61B 5/4845* (2013.01); *H01J 49/0427* (2013.01)

(58) Field of Classification Search
USPC .............. 250/281, 282, 288; 73/19.01, 19.02, 73/23.2, 23.3
See application file for complete search history.

(56) References Cited

U.S. PATENT DOCUMENTS 4,292,978 A    10/1981   Guth
5,042,501 A    8/1991    Kenny et al.
(Continued)

FOREIGN PATENT DOCUMENTS

DE    19718924 A1    10/1998
EP    0997733         5/2000
(Continued)

OTHER PUBLICATIONS

Beck et al. "Demonstration that methadone is being present in the exhaled aerosol breath fraction", Aug. 9, 2011, Journal of Pharmaceutical and Biomedical Analysis, 56 (2011) pp. 1024-1028.*
(Continued)

*Primary Examiner* — Nicole Ippolito
(74) *Attorney, Agent, or Firm* — Downs Rachlin Martin PLLC (57) ABSTRACT

A method recovering one or more nonvolatile compounds from an exhaled aerosol collected on an electrostatic filter membrane (205) comprises eluting the nonvolatile compounds from the filter with a polar solvent and collecting the eluate. The method is useful for processing samples collected from a portable breath analysis device comprising a sampling filter membrane for analysis.

18 Claims, 4 Drawing Sheets

(51) Int. Cl.
*A61B 5/08* (2006.01)
*A61B 5/097* (2006.01)
*A61B 5/00* (2006.01)
*H01J 49/04* (2006.01)

(56) References Cited

U.S. PATENT DOCUMENTS

| | | |
|---|---|---|
| 5,195,527 A | 3/1993 | Hicks |
| 5,465,728 A | 11/1995 | Phillips |
| 5,467,776 A | 11/1995 | Hamilton |
| 5,478,377 A | 12/1995 | Scavnicky et al. |
| 5,721,102 A | 2/1998 | Vo-Dinh |
| 5,834,626 A | 11/1998 | De Castro |
| 6,097,480 A | 8/2000 | Kaplan |
| 6,209,541 B1 | 4/2001 | Wallace |
| 6,623,977 B1 | 9/2003 | Farquharson et al. |
| 7,450,227 B2 | 11/2008 | Dwight et al. |
| 8,368,883 B2 | 2/2013 | Palmskog et al. |
| 8,705,029 B2 | 4/2014 | Palmskog et al. |
| 2002/0095078 A1 | 7/2002 | Mannheimer et al. |
| 2002/0177232 A1 | 11/2002 | Melker et al. |
| 2003/0028120 A1 | 2/2003 | Mault et al. |
| 2005/0048660 A1 | 3/2005 | Bearer |
| 2005/0051719 A1 | 3/2005 | Miller et al. |
| 2005/0065446 A1 | 3/2005 | Talton |
| 2005/0137491 A1 | 6/2005 | Paz et al. |
| 2005/0233459 A1 | 10/2005 | Melker et al. |
| 2006/0038990 A1 | 2/2006 | Habib et al. |
| 2006/0084182 A1 | 4/2006 | Farquharson et al. |
| 2006/0119853 A1 | 6/2006 | Baumberg et al. |
| 2006/0153740 A1 | 7/2006 | Sultan et al. |
| 2006/0266353 A1 | 11/2006 | Yamada et al. |
| 2007/0023627 A1 | 2/2007 | Finch et al. |
| 2007/0156211 A1 | 7/2007 | Ferren et al. |
| 2007/0224128 A1 | 9/2007 | Dennis et al. |
| 2007/0252077 A1 | 11/2007 | Shoji |
| 2007/0258894 A1 | 11/2007 | Melker et al. |
| 2008/0183388 A1 | 7/2008 | Goodrich |
| 2012/0212735 A1 | 8/2012 | Palmskog et al. |
| 2012/0302907 A1* | 11/2012 | Palmskog et al. ............ 600/532 |
| 2013/0066223 A1 | 3/2013 | Beck et al. |
| 2013/0128260 A1 | 5/2013 | Palmskog et al. |
| 2014/0366609 A1* | 12/2014 | Beck et al. .................... 73/23.3 |
| 2015/0033824 A1* | 2/2015 | Hammarlund et al. ....... 73/23.3 |

FOREIGN PATENT DOCUMENTS

| | | |
|---|---|---|
| EP | 2518499 | 10/2012 |
| JP | H04507204 | 12/1992 |
| JP | 2001-505660 A | 4/2001 |
| JP | 2004-301749 A | 10/2004 |
| JP | 2007-525670 A | 9/2007 |
| JP | 2008102048 | 1/2008 |
| JP | 2009-047593 A | 3/2009 |
| WO | 0184112 | 11/2001 |
| WO | 03057521 | 7/2003 |
| WO | 2005098429 | 10/2005 |
| WO | 2009030957 | 3/2009 |
| WO | 2009045163 | 4/2009 |
| WO | 2011029888 | 3/2011 |

OTHER PUBLICATIONS

Almstrand, Ann-Charlotte et al: "Airway monitoring by collection and mass spectrometric analysis of exhaled particles", Analytical Chemistry, American Chemical Society, vol. 81, No. 2, Jan. 15, 2009, pp. 662-668, XP007915715; ISSN: 0003-2700.

Beck, O et al., "Method for determination of methadone in exhaled breath collected from subjects undergoing methadone maintenance treatment," Journal of Chromatography B: Biomedical Sciences & Applications, Elsevier, Amsterdam, NL., Jul. 3, 2010, pp. 2255-2259, vol. 878, No. 24.

Beck, Olof et al., "Study on the sampling of methadone from exhaled breath", Journal of Analytical Toxicology, vol. 35, No. 5, Jun. 2011, pp. 257-263, XP55045425.

Bernd Sagmuller et al, Application of SERS Spectroscopy to the identification of (3,4-methylenedioxy) Amphetamine in Forensic Samples Utilizing Matrix Stabilized Silver Halides, Oct. 2001, pp. 2066-2071, vol. 126, No. 11, The Analyst, The Royal Society of Chemistry 2001.

Buszewski Boguslaw et al., "Human exhaled air analytics: biomarkers of diseases," Biomedical Chromatography, Jun. 2007, pp. 553-566 & 588, vol. 21, No. 6.

EPO Communication re Personal Consultation with Examiner, dated Dec. 10, 2012, issued in connection with related EP10751947.2.

EPO Communication, Article 94(3) dated Mar. 7, 2013, issued in connection with related EP10751947.2.

EPO Communication, Article 94(3) dated Oct. 23, 2012, issued in connection with related EP10751947.2.

European Search Report dated Jun. 8, 2011, in connection with related EP Application No. 11157565.

Extended European Search Report dated Apr. 11, 2012, in connection with related EP Application No. 12 15 8911.

Fabian, Patricia et al., "Influenza virus in human exhaled breath: an observational study", PLOS One 2008, vol. 3, No. 7, Jul. 16, 2008, p. e2691, XP7921865, ISSN: 1932-6203.

International Preliminary Report on Patentability dated Oct. 27, 2011, in connection with related PCT/EP2010/063265 filed Sep. 9, 2010.

International Search Report and Written Opinion dated Nov. 19, 2010, for related application PCT/EP2010/063266 filed Sep. 9, 2010, entitled "Drug Detection in Exhaled Breath," Palskog, G et al.

International Search Report dated Nov. 24, 2010, in connection with related PCT/EP2010/063265 filed Sep. 9, 2010.

International Search Report dated May 23, 2013, in connection with related PCT/EP2013/054789, filed Mar. 8, 2013.

Marks, P, "Taking on the drugged and drunk drivers," New Scientist, Reed Business Information, Surrey, GB, vol. 188, No. 2528, Dec. 3, 2005, pp. 28-29.

Miekisch, W et al., "Assessment of propofol concentrations in human breath and blood by means of HS-SPME-GC-MS," Clinica Chimica Acta, Elsevier BV, Amsterdam, NL, Sep. 1, 2008, pp. 32-37, vol. 395, No. 1-2.

Mutlu G. M., et al., "Collection and analysis of exhaled breath condensate in Humans", American Journal of Respiratory and Critical Care Medicine, American Lung Association, NY, NY, vol. 164, 2001, pp. 731-737, XP003012811, ISSN: 1073-449X.

Sagmuller et al., Application of SERS spectroscopy to the identification of (3,4-methylenedioxy)amphetamine in forensic samples utilizing matrix stabilized silver halides, Analyst, Royal Society of Chemistry, GB, vol. 126, No. 11, Nov. 1, 2001, pp. 2066-2071.

Sanchez, C et al., "Determination of Nitroaromatic Compounds in Air Samples at Femtogram Level Using C18 Membrane Sampling and On-line Extraction with LC-MS," Analytical Chemistry, Sep. 1, 2003, pp. 4639-4645, vol. 75, No. 17.

Sulk et al., Surface-Enhanced Raman Scattering Detection of Amphetamine and methamphetamine by Modification with 2-Mercaptonicotinic Acid, Applied Spectroscopy, the Society for Applied Spectroscopy, Baltimore, US, vol. 53, No. 8, Jan. 1, 1999, pp. 954-959.

Written Opinion dated Apr. 11, 2012, in connection with related EP Application No. 12 15 8911.

Written Opinion dated Jun. 8, 2011, in connection with related EP Application No. 11157565.

Written Opinion dated May 23, 2013, in connection with related PCT/EP2013/054789, filed Mar. 8, 2013.

Office Action dated Oct. 21, 2013, in connection with related Japan Application No. Tokugan-2012-528364.

Office Action dated Nov. 14, 2014, in connection with related U.S. Appl. No. 13/394,609, filed May 29, 2012.

Office Action dated Aug. 2, 2013, in connection with related U.S. Appl. No. 13/739,607, filed Jan. 11, 2013.

Response to Office Action dated Dec. 2, 2013, in connection with related U.S. Appl. No. 13/739,607, filed Jan. 11, 2013.

Office Action dated Aug. 13, 2014, in connection with related U.S. Appl. No. 13/416,956, filed Mar. 9, 2012.

(56) References Cited

OTHER PUBLICATIONS

Response to Office Action dated Jan. 13, 2015, in connection with related U.S. Appl. No. 13/416,956, filed Mar. 9, 2012.
International Search Report dated Apr. 2, 2012, issued in connection with related PCT/EP2012/054180, filed: Mar. 9, 2012.
Written Opinion dated Apr. 2, 2012, issued in connection with related PCT/EP2012/054180, filed: Mar. 9, 2012.
Periago, J. F. et al.; "Design and evaluation of an exhaled breath sampler for biological monitoring of organic solvents," Journal of Applied Toxicology, vol. 12, No. 2, Apr. 1, 1992; pp. 91-96; ISSN: 0260-437X.
Written Opinion dated Jul. 3, 2014 in connection with related EP14164314.8, filed Sep. 9, 2010.
European Search Report dated Jul. 3, 2014 in connection with related EP14164314.8, filed Sep. 9, 2010.
Zwir-Ferenc, A., et al., Solid Phase Extraction Technique—Trends, Opportunities and Applications; Polish J. of Environ. Stud., vol. 15, No. 5 (2006); pp. 677-690.
Response to Office Action dated May 14, 2015, in connection with related U.S. Appl. No. 13/394,609, filed May 29, 2012.
Final Office Action dated Jun. 19, 2015, in connection with related U.S. Appl. No. 13/394,609, filed May 29, 2012.
Response to Final Office Action dated Aug. 19, 2015, in connection with related U.S. Appl. No. 13/394,609, filed May 29, 2012.
Advisory Action dated Sep. 2, 2015, in connection with related U.S. Appl. No. 13/394,609, filed May 29, 2012.
Final Office Action dated Apr. 28, 2015, in connection with related U.S. Appl. No. 13/416,956, filed Mar. 9, 2012.
Response to Final Office Action dated Jun. 29, 2015, in connection with related U.S. Appl. No. 13/416,956, filed Mar. 9, 2012.
Advisory Action dated Jul. 24, 2015, in connection with related U.S. Appl. No. 13/416,956, filed Mar. 9, 2012.
Office Action dated Apr. 22, 2015, in connection with related Russian Patent Application No. 201391293/31, filed Nov. 21, 2013.
International Search Report dated Oct. 4, 2013, in connection with related PCT/EP2013/068860, filed Sep. 11, 2013.
Written Opinion dated Oct. 4, 2013, in connection with related PCT/EP2013/068860, filed Sep. 11, 2013.
Olof Beck et al., "Demonstration that methadone is being present in the exhaled breath aerosol fraction", Aug. 3, 2011, Journal of Pharmaceutical and Biomedical Analysis, pp. 1024-1028, ISSN: 0731-7085.
Olof Beck et al., "Amphetamines detected in exhaled breath from drug addicts: A new possible method for drugs-of-abuse testing", Journal of Analytical Toxicology, vol. 34, No. 5, Jun. 2010, pp. 233-237; ISSN: 0146-4760.
Amendment and Response filed with RCE dated Oct. 28, 2015, in connection with U.S. Appl. No. 13/416,956, filed Mar. 9, 2012.
Office Action dated Dec. 17, 2015, in connection with U.S. Appl. No. 14/222,696, filed Mar. 24, 2014.
Amendment filed with RCE dated Dec. 21, 2015, in connection with U.S. Appl. No. 13/394,609, filed May 29, 2012.
Office Action dated Feb. 17, 2016 related to U.S. Appl. No. 13/394,609, filed May 29, 2012, Goran Palmskog.
Office Action dated Feb. 1, 2016 related to U.S. Appl. No. 13/416,956, filed Mar. 9, 2012, Olof Beck.

\* cited by examiner

SYSTEM AND METHOD FOR ELUTING AND TESTING SUBSTANCE FROM EXHALED AEROSOL SAMPLE

FIELD OF THE INVENTION

The present invention relates to methods for eluting nonvolatile compounds from a solid matrix. In particular, the invention is a method for eluting and optionally analyzing nonvolatile compounds collected on a membrane from exhaled air.

BACKGROUND OF THE INVENTION

Exhaled breath is commonly used in alcohol testing and today's technology makes it possible to perform on-site breath testing with legally defensible results using infrared spectroscopy.

Testing DNA and testing for drugs, whether abused or used therapeutically, generally requires the taking of blood or urine samples for testing. Hair, sweat, and oral fluid can also used for drug and DNA testing. Blood sampling is invasive and requires medically trained personnel, and the test subject is often transported to a hospital or other specialized facility for sampling. These procedures are time and effort consuming. The collection of urine samples may also be considered intruding on personal integrity. Other problematic issues related to samples and specimens taken from a subject include risk of disease transmission or infection and the risk of the subject exchanging samples or using a clean sample from another subject to avoid detection of illicit drugs.

The need to provide a non-invasive, not-specimen based apparatus, system and/or method for detecting the presence (i.e. qualitative) or determining the quantitative amount of a substance in a subject is at least partially met by the invention disclosed in PCT Application No. PCT/EP2012054180, the contents of which are incorporated herein by reference for all purposes. PCT/EP2012054180 discloses an apparatus, system and method for sampling the exhaled breath of a subject for a drug substance and/or a biomarker. Aerosols from the lungs of the subject are collected on a sampling membrane and then analyzed for the presence and optionally the amount of one or more nonvolatile compounds.

In DE19718924, breath is in a specific exhalation device conveyed through a fiber fleece. Large aerosol particles are caught in the fiber fleece by condensation. The device of DE19718924 comprises several valves which increase the resistance to blow through the device. The fiber fleece is removed from the housing, folded into the upper part of a centrifugal tube. The fiber fleece can be contaminated by this procedure. A standard elution solution, such as ELISA buffer or salt solutions, is added to the tube. A total amount of lung substances from the caught aerosol is determined from the eluate obtained. The determined total amount of lung substances allows for diagnosis and therapy of diseases, such as asthma. However, the disclosure of DE19718924 is not very detailed. The total amount of lung substances obtained as a result is not very specific and allows only coarse diagnostics and doubtful therapy based on such diagnostics. Sampling times in a range of 5-15 minutes are rather long and consistency of results over the range is not demonstrated. The method and device of DE19718924 do not appear to be very efficient and have a limited applicational range. Despite DE19718924 being published in 1998, no major improvement has been disclosed during 15 years. Hence a long felt need exists for improvement.

The present invention provides a method for eluting nonvolatile compounds from a sampling membrane in such a way that the eluted compounds are easily assayed. The present method improves the yield and consistency of recovery of nonvolatile compounds from sampling membranes used to collect aerosols from exhaled breath.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a method, according to the appended patent claims.

According to one aspect of the invention, a method for recovery is provided for collecting nonvolatile compounds from a sample taken from the exhaled breath of a subject for further analysis. The method may comprise removing a sampling membrane from a housing of a breath sampling device. Alternatively, the sampling membrane may be in place in a housing of a breath sampling device. Nonvolatile compounds may be eluted by passing a polar solvent through an inlet and an outlet in an adapted housing. By leaving the sampling membrane in place and eluting through the housing lowers the risk of contamination of the membrane. It also provides a more convenient and fast way of handling a collected breath sample.

A sampling membrane comprising collected from exhaled breath and aerosols containing nonvolatile compounds of interest is eluted by passing a polar organic solvent through the membrane using gravity alone or under pressure or centrifugal force.

In some examples of the invention, the sampling membrane is a filter membrane, preferably an electrostatic filter membrane, and most preferably an electrostatic membrane comprising nonwoven acrylic and polyethylene fibers.

The sampling membrane may be a filter membrane comprising at least one layer of non-woven filtration media with a specific weight in the range of 23 g/m3 to 500 g/m3, preferably in the range of 150 up to 300 g/m3, and even more preferably in the range of 200 up to 280 g/m3 and may comprise at least one further layer that is a spunbonded carrier with a scrim weight of 10 to 20 g/m3.

The polar solvents suitable for use in the method are miscible in water, are capable of dissolving water soluble and lipid soluble components of the exhaled aerosol, and are capable of eluting the nonvolatile compounds of interest. Polar solvents meeting these criteria include methanol, acetonitrile, isopropanol, and acetone.

The nonvolatile compounds of interest may originate from blood by a mechanism of producing a gas phase in the alveoli or from other parts of the airways and are transferred from the lungs carried by an aerosol. The nonvolatile compounds may be medical drugs, drugs of abuse, metabolites of drugs, markers indicative of drug use, or naturally occurring markers of disease states or metabolic conditions of subjects. Analysis of nonvolatile compounds from sample membranes may include mass-spectroscopy (MS) and Surface Enhanced Raman Spectroscopy (SERS) and other sensitive analytical methods known in the art.

In some examples of the invention, the aerosol on the sampling membrane may contain nonvolatile compounds of at least one drug substance in the exhaled breath. Nonlimiting examples of drug substances include amphetamines, ecstasy, Cannabis, THC, cannabinoids, opiates, heroin, morphine, 6-AM, cocaine, benzodiazepines, Propoxyphene, Methadone, Buprenorphine, Tramadol, LSD, Designer/Internet drugs, Kathinon, GHB, Meprobamat, Z-drugs, tryptamines, and anabolic steroids.

MS and SERS are the preferred analyzing methods with liquid chromatography/MS (LC/MS) being preferred over gas chromatography/MS (GC/MS).

Further examples of the invention are defined in the dependent claims, wherein features for the second and subsequent aspects of the invention are as for the first aspect mutatis mutandis.

Some known nonvolatile biomarker that may be transported by aerosols in exhaled breath is comprised in the list comprising lipids, peptides, nucleotides, prostanoids, proteins, DNA or RNA. These biomarkers may be used for diagnosis of diseases or illnesses, such as cancer (such as lung cancer), asthma, inflammation, infection (such as tuberculosis) and/or oxidative stress or other medical conditions.

The term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the invention are capable of will be apparent and elucidated from the following description of examples of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 1:
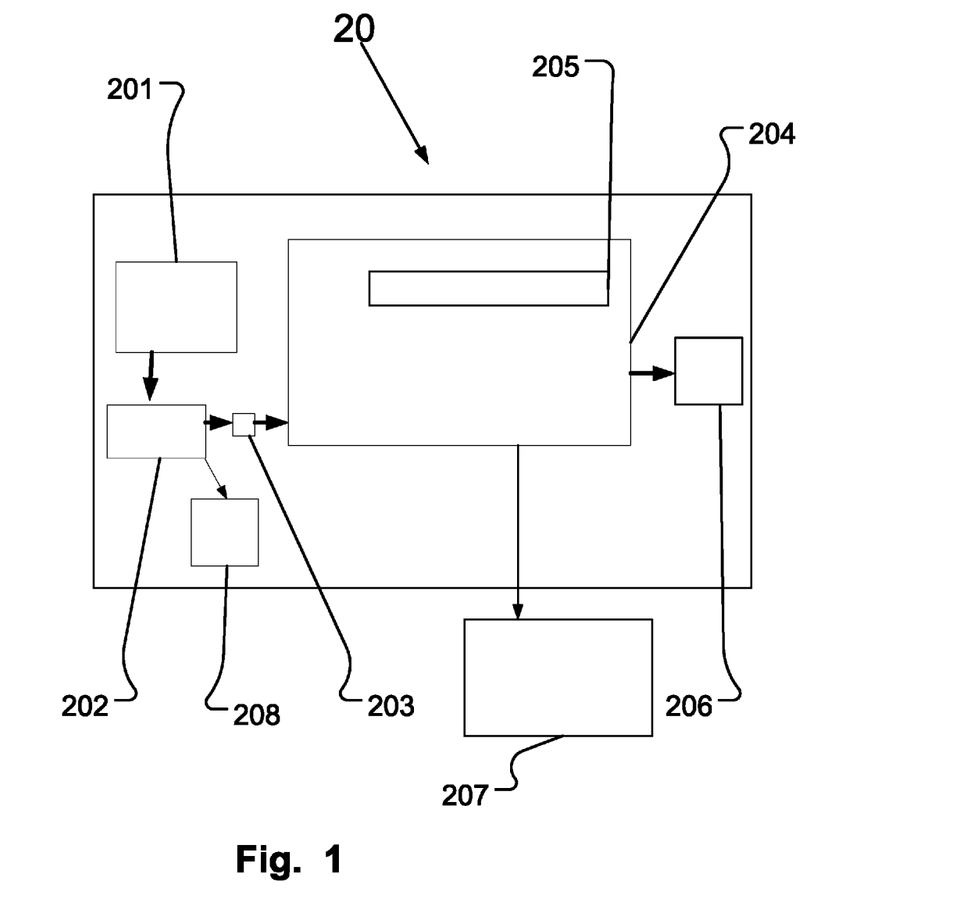
FIG. 1 is a schematic illustration illustrating an example of a portable device configured to collect a sample from exhaled breath of a subject.
Figure 2:
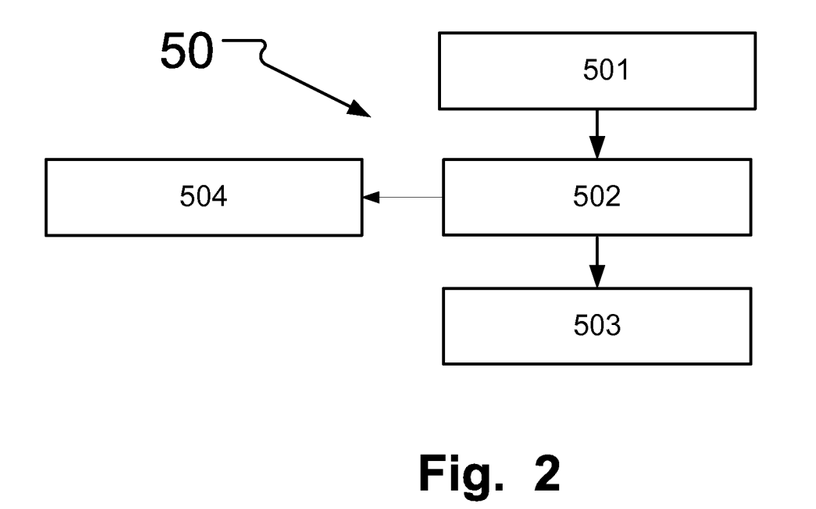
FIG. 2 is a flow-chart illustrating a method for using a portable device configured to collect a sample from exhaled breath of a subject.

In FIG. 1 is a schematic illustration showing an example of a portable system configured to collect a sample from exhaled breath of a subject. Sampling system 20 is configured to collect a sample from exhaled breath of a subject 201. The subject exhales through a mouthpiece and a tubular element 202 being in flow communication with a housing 204 via at least one inlet 203. The mouthpiece and tubular element 202 may be of same size or type as conventionally used for alcohol-testing. Preferably, the mouthpiece and tubular element 202 are configured to mainly permit aerosols to pass through.

The housing 204 can be made of any suitably material or combinations thereof such as, metal, plastic, glass or ceramics and comprises a sampling membrane 205, being a fibre membrane, for collecting aerosols comprising non-volatile drug substances from the exhaled breath. The exhaled breath exits the housing through at least one outlet 206. The portable system may be sealed after being used and sent to a laboratory 207 to be analyzed. Analysis of the amount of illicit drugs may be performed using any suitable method with Surface Enhanced Raman Spectroscopy (SERS) and mass-spectroscopy (MS), for example Liquid chromatography MS (LCMS), being most preferred.

The sampling membrane can be placed anywhere in the housing 204. Preferably the sampling membrane 205 is fastened to the inner walls of the housing 204 and stretched over the cross-section of the housing. The housing 204 is preferably constructed out of two or more parts, a first part with an inlet 203 and one part with at least one outlet 206.

The mouthpiece and tubular element 202 are detachable and in fluid communication with the housing 204 via the inlet 203. The tubular element 202 functions as a pre-filter for filtering out saliva and/or mucus and/or large particles and/or aggregates from the exhaled breath. Thus a cleaner sampling membrane, such as a filter membrane, to be analyzed is obtained, which may result in better and more accurate analysis. Another advantage of using a tubular element 202 is to prevent contamination between subjects and samples.

The exhaled breath will, after flowing through the tubular element 202, travel into the housing 204 and be brought into contact with the sampling membrane 205, preferably a filter membrane.

The drug substances, being non-volatile compounds conveyed by aerosols in the exhaled breath, are collected by the sampling membrane 205 as the exhaled breath is permeated through the sampling membrane 205.

The sampling membrane 205, being a filter membrane is not to be confused with an electronic or chemical sampling unit and/or trap. The sampling element 205 is a physical entity on which the drug substance is collected. Collection may, in different embodiments, be based on various principles, singly or in combination, comprising depositing, catching, fastening, and condensing of non-volatile constituents on the sampling element 205.

Using a filter membrane allows for a low pressure drop through the portable sampling system, making it easy and comfortable to exhale through the device. This is important for subjects experiencing problems with their lungs.

In an example of a portable sampling system, the filter membrane is placed to block the path for the exhaled breath through the portable system.

There are many possibilities for fastening the filter membrane, for example, using a separate support structure to retain the filter, which may be an element that is either fastened to the inside walls of the housing 204 or a segment being slid onto a first part of the housing during the assembly before the second part of the housing is mounted.

Alternatively and/or additionally, the filter membrane may be fastened direct onto the inside walls of the housing 204, either by glue or by heat and thereby melting a small part of the edge of the filter membrane.

The second part of the housing is either screwed or slid onto the first part of the housing. The second part comprises at least one outlet 206. Alternatively and/or additionally, the housing 204 may comprise at least two outlets 206. This will aid to avoid a subject being tested to block the outlet and thereby blowing up the volume measuring element with minimum exhaled breath being permeated through the filter membrane The sampling element 205 is preferably a filter membrane made of synthetic and/or half-synthetic fibers for the exhaled breath to diffuse through. The filter membrane has a structure that catches the aerosols and thereby collects the drug substances being exhaled while letting gas pass through. The aerosol particles comprise the non-volatile drug compounds. Preferably, the filter membrane is operable to collect the aerosols from the air with a high volumetric capacity while maintaining a low pressure drop across the filter substrate. Alternatively and/or additionally, in some examples the filter membrane may be an electrostatic filter made of fibers. Alternatively and/or additionally, the filter membrane may be of a non-woven polymeric fibrous that may be an electret.

Alternatively and/or additionally, the filter membrane may be an electrostatic filter being preferably a non-woven filter membrane comprising a blend of acrylic fibers and polypropylene fibers. The filter membrane may have a density (sometimes called grade or weight) in the range 23 up to 500 g/m2. But it has been shown that the range 130 up to 300 g/m2 is preferred. Even more preferably is the range 200 up to 280 g/m2.

Alternatively and/or additionally, the non-woven layer may be attached to at least one further layer. Further layers can be used to enhance a filter membrane's physical properties or improve filtration performance. The extra layer can be a carrier, preferably a polypropylene spunbonded carrier. The spunbond carrier may have a scrim weight in the range 10 up to 20 g/m2, preferably 15 g/m2.

For example a three layered filter membrane comprising one non-woven layer with a density of 250 g/m2 and two layers being carriers each with a scrim weight of 15 g/m2 will have an air flow resistance of about 36 Pa at 9.5 m/min media velocity. Alternatively and/or additionally, the filter membrane may be corrugated to enhance the filtering area within a given housing volume.

The portable system combined with the method of eluting the content of the filter membrane is configured and adapted to have a sensitivity for illicit drugs high enough to obtain results of a standard to be used as proof in a court of law.

The collected aerosols may comprise nonvolatile compounds of at least one drug substance in the exhaled breath. The drug substance may, by way of example, be an amphetamine, ecstasy, Cannabis, THC, a cannabinoid, an opiate, heroin, morphine, 6-AM, cocaine, a benzodiazepine, Propoxyphene, Methadone, Buprenorphine, Tramadol, LSD, a designer/Internet drug, Kathinon, GHB, Meprobamat, a Z-drug, a tryptamine, or an anabolic steroid. Other illicit drugs (drugs of abuse) and therapeutic drugs not included in the list may also be detectable due to similar interchanges with the human body as the above mentioned illicit drug substances.

Alternatively and/or additionally, non-volatile compounds may include biomarkers transported by aerosols in exhaled breath. These biomarkers may comprise lipids, peptides, nucleotides, prostanoids, proteins, DNA or RNA and may be used for diagnosis of diseases or illnesses, such as cancer (such as lung cancer), asthma, inflammation, infection (such as tuberculosis) and/or oxidative stress or other medical conditions. These biomarkers may be collected and recovered using the system and methods described herein.

FIG. 2 is a flow-chart illustrating a method 50 for using a portable system configured for collecting a sample 502 from exhaled breath from a subject. Briefly, FIG. 2 illustrates detecting the presence and/or determining the quantitative amount 503 of at least one illicit drug substance or compound in a collected sample. The illicit drug compounds are collected as aerosols, being non-volatile particles and/or compounds, from the exhaled breath. The method comprises: a subject exhaling 501 into the invented portable system; a sampling unit collects a sample 502 comprising drug substances or compounds; the collected sample is extracted from the sampling membrane and analyzed 503 using MS or SERS.

With reference to FIG. 2, a subject exhales 501 in and out; preferably the subject exhales into the portable system until a specific volume of exhaled breath has been passed through the sampling membrane, preferably a filter membrane.

Alternatively and/or additionally, the subject may exhales either for a certain time or for a fixed number of times, such as 1 to 10 times, into a portable system. When breathing a fixed number of times, each exhalation may be set to last for a fixed time.

To measure a specific volume, one preferred method is to use a port located on the mouthpiece or between the mouthpiece and the inlet of the housing. A portion of the exhaled breath is extracted 504 through the port and inflates an element, such as a non-elastic bag. Hence when the bag is full, the volume of said bag will be proportional to the volume passed through the sampling membrane.

Alternatively and/or additionally, a bag with elastic properties may be used.

A deep breath is preferred to obtain exhaled breath from deep lying lung portions, such as the central or peripheral lung regions.

The exhaled breath is then collected 502 by the sampling element, i.e. an easy to breathe through filter membrane, suitable for collecting drug substances before it exits the system. The filter membrane is preferably made of synthetics and/or half synthetic fibers. Preferably, the filter membrane has electrostatic-properties. Using a filter membrane creates a small, light-weight and easy to use method that can be used everywhere by anyone to detect if a subject is under influence of an illicit drug. The sampling method is of such high quality that the obtained results are of a court approved standard. These results are obtained using a method that is neither invasive, e.g. Blood sampling, nor intruding on personal integrity, e.g. urine sampling. Hence the known drawbacks with these methods are prevented.

After being used, the housing of the sampling system is sealed off by sealing the inlet and the outlet and the device may be sent to a laboratory, where the collected compounds in the filter are recovered an analyzed.

FIG. 3 illustrates a method 30 for recovering one or more nonvolatile compounds from a sampling filter membrane. The fibers are preferably nonwoven and filter is most preferably a felt or a matted material. The filter is preferably an electrostatic filter and most preferably comprises acrylic fibers and polypropylene fibers. The method comprises contacting 301 the filter with an amount of a polar solvent capable of neutralizing the electrostatic charge on the filter. The contacting of the filter with the polar solvent elutes the nonvolatile compounds from the sampling filter to form an eluate. Preferred polar solvents include methanol, acetonitrile, isopropanol, acetone, and combinations thereof, with methanol and acetonitrile being most preferred for their relative ease of handling. The polar solvents are miscible in water, are capable of dissolving water soluble and lipid soluble components of the aerosol, and thereby eluting the nonvolatile compounds of interest from the filter membrane. Polar solvents meeting these criteria include methanol, acetonitrile, isopropanol, and acetone. Methanol and acetonitrile are preferred polar solvents in combination with filter membranes comprising acrylic and polyethylene fibers. Preferably, the polar solvents are used in pure form, i.e. in no mixture with other compounds or solvents. Pure solvents are e.g. pure methanol, or pure acetonitrile.

The amount of solvent used depends on the size of the filter and should be enough to elute the nonvolatile compounds but should not unnecessarily dilute the compounds. By way of example, the amount of solvent may be between 0.02 ml and 20 ml. Contacting may be accomplished by washing the filter with the solvent, for example by passing an amount of the solvent through the filter. The filter 205 is preferably in the housing 204 of the sampling device with the solvent being passed though the device from one of the inlet 203 or outlet 206 to the other of the inlet 203 or outlet 206 of the device. Alternatively, the filter 205 may be removed from the device and placed in a column for elution with the solvent by gravity or with pressure. The filter may alternatively be soaked in the solvent before being placed in a centrifuge tube or column.

Figure 3:
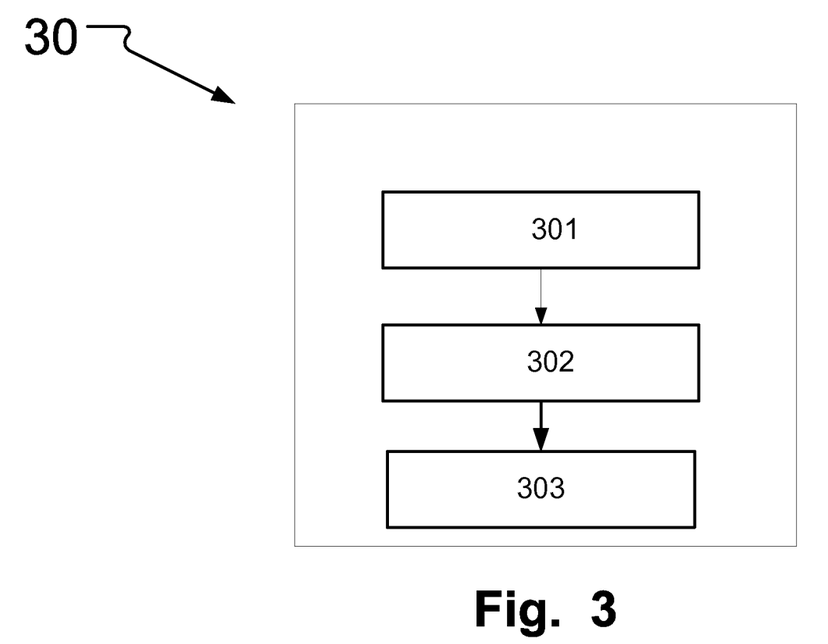
FIG. 3 is a flow chart of method steps for a recovery method according to the invention.

After the solvent is contacted with the filter membrane, the eluate is collected 302 in a suitable container. Collection may be accomplished, for example, by gravity flow from a filter in a device or, alternatively, saturating the filter with solvent and placing the device in a centrifuge with a collecting vessel positioned to receive the eluate during centrifugation. The eluate may also be collected by applying solvent to a sampling device and applying pressure to force the solvent through the filter and into a collecting vessel. Collection may also be accomplished by gravity, pressure, or centrifugation from a filter that has been removed from a sampling device and placed in a column or tube for elution by gravity, pressure, or centrifugation.

The collected eluate may be stored or optionally delivered 303 to an assay system capable of detecting (qualitative analysis) and/or measuring (quantitative analysis) one or more nonvolatile compounds in the eluate. Any suitable assay system may be used, with LC/MS, GC/MS, and SERS being most preferred. MS may include, for example, time-of-flight MS, quadrupole ion trap MS, tandem MS, electrospray ionization MS, and matrix-assisted laser desorption/ionization MS. Depending on the assay system being used, the eluate may be pretreated or concentrated before delivery to the assay system. For LC/MS, the eluate may be loaded into the liquid chromatography column, optionally after reducing the volume of the eluate by evaporation of the solvent with or without partial vacuum. For SERS, the eluate may be placed on a SERS substrate comprising, for example, gold or silver colloids, optionally after reducing the volume of the eluate. The eluate may alternatively be evaporated to dryness to form a dry residue that is resuspended in the same or a different solvent or combination of solvents before application to an assay system.

Figure 4:
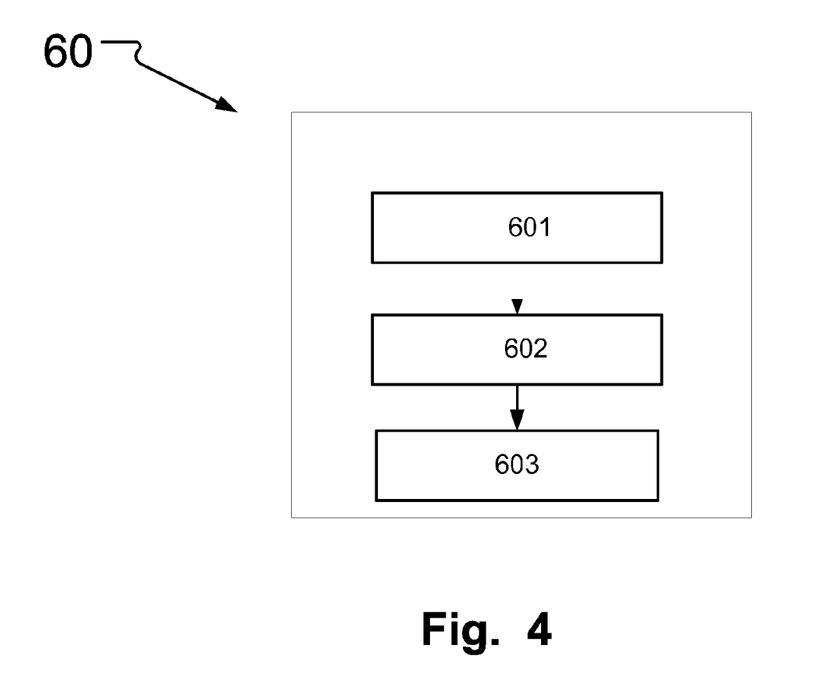
FIG. 4 illustrates a system for detecting the presence or determining the quantitative amount of at least one drug compound in exhaled breath.

FIG. 4 illustrates a system 60 for detecting the presence or determining the quantitative amount of at least one drug compound in exhaled breath. The system comprising a portable drug testing device 602 for handheld collection of a sample from exhaled breathe from a subject 601. The device 602 could be according to any embodiment described herein. Further, the system 60 comprises a sensor unit 603 for analyzing the collected compounds in the testing device 602. The sensor could be any know type of sensor but preferably mass spectroscopy or SERS. To be able to analyze the collected sample the content of the filter membrane in the device 602 is extracted. This could be done for example by using a solvent to be analyzed using the sensor unit 603.

An advantage is that the test may be performed almost anywhere at a low cost and short lead time before obtaining a result.

Example 1

Figure 5:
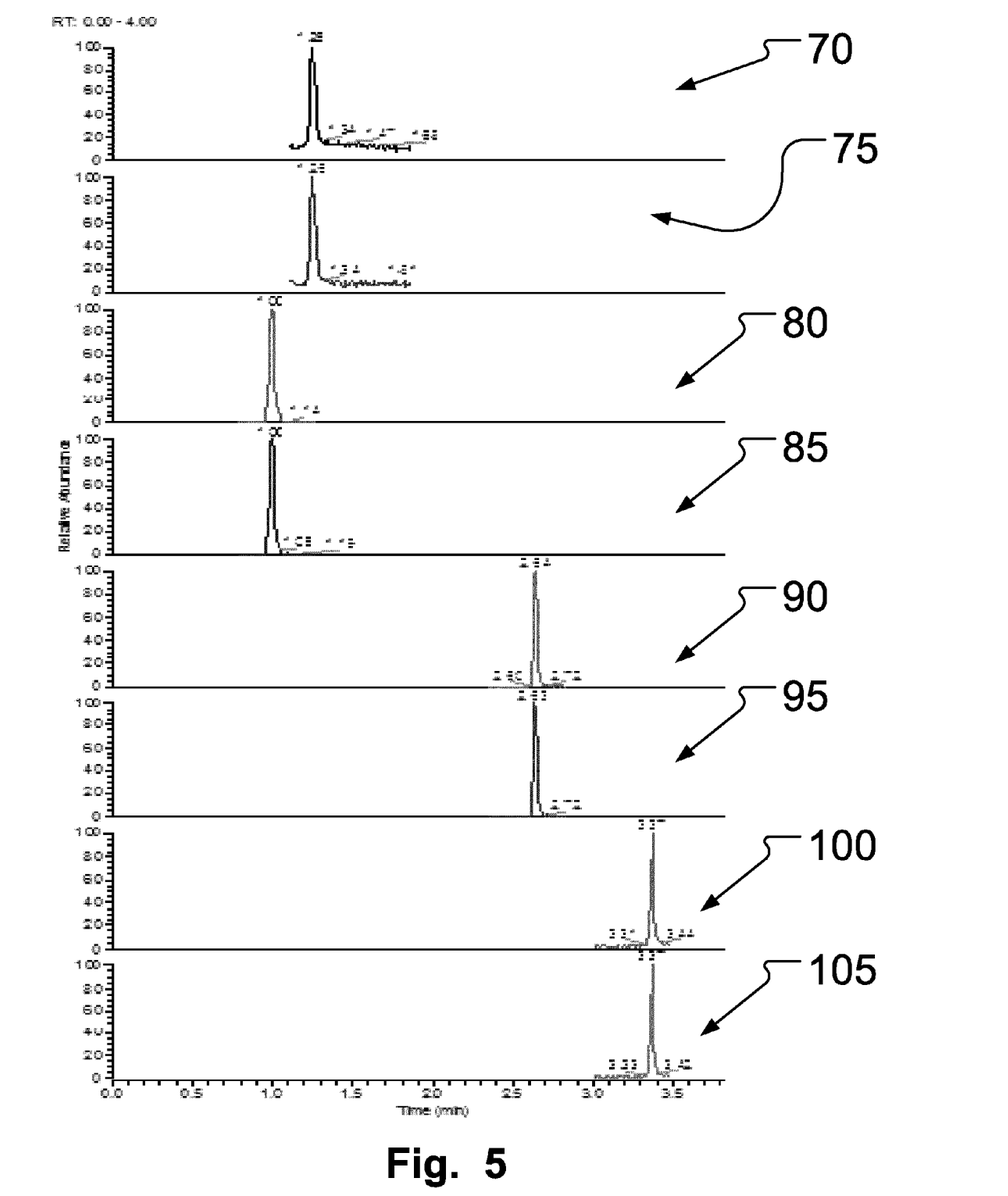
FIG. 5 illustrates typical chromatograms for four different drugs.

Table 1 shows the results of recovering a variety of non-volatile compounds from an electrostatic filter membrane comprising acrylic fibers and polyethylene fibers by elution with methanol. The eluates were analyzed using LC-MS/MS with reference solution. Recovery and assay for each nonvolatile compound analyte was performed in triplicate. Typical chromatograms for some drugs when analyzing the eluates using LC-MS/MS equipment are illustrated in FIG. 5. From the top to the bottom the chromatogram shows peaks for, amphetamine 70, 75; Morphine 80, 85; Diazepam, 90, 95; and THC, 100, 105. As there is a linear relation between concentration (pg/filter) and the area ratio of analyte to internal standard for all compounds the amount of drug in the filter may be determined based on calibration curves from reference solutions.

TABLE 1

Recovery of nonvolatile compounds by methanol elution

| Analyte | Recovery (%) | Analyte | Recovery (%) |
|---|---|---|---|
| Amphetamine | 101 | Methamphetamine | 107 |
| THC | 95 | Morphine | 98 |
| Codeine | 97 | MDMA | 93 |
| Benzoylecgonine | 95 | Cocaine | 95 |
| Buprenorphine | 116 | Methadone | 115 |
| Oxazepam | 106 | Flunitrazepam | 107 |
| 6-Acetylmorphine | 97 | Diazepam | 105 |

The present invention has been described above with reference to specific embodiments. However, other alternatively and/or additionally embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A method for recovery of non-volatile compounds from an electrostatic filter membrane, wherein said electrostatic filter membrane is fitted in a housing comprising at least one inlet and at least one outlet and wherein said housing is part of a sampling system for exhaled breath, the method comprising:
    providing said electrostatic filter membrane containing an exhaled aerosol comprising a nonvolatile compound;
    washing said electrostatic filter membrane with a polar organic solvent to form an eluate;
    collecting said eluate comprising said nonvolatile compound; and
    pouring said solvent in one of said inlet or outlet and collecting said eluate through the other of said inlet or outlet.

2. The method according to claim 1, wherein said filter membrane comprises at least one layer of non-woven filtration media with a specific weight in the range of 23 g/m3 to 500 g/m3.

3. The method according to claim 2, wherein said electrostatic filter membrane comprises at least one further layer, said further layer being a spunbonded carrier with a scrim weight of 10 to 20 g/m3.

4. The method according to claim 2, wherein said electrostatic filter membrane has a filter surface to be passed by exhaled gas of approximately 800 mm2 and a pressure drop of 36 Pa at 9.5 m/min media velocity.

5. The method according to claim 1, wherein said electrostatic filter membrane comprises a blend of acrylic fibers and polypropylene fibers.

6. The method according to claim 1, wherein said aerosols comprise nonvolatile compounds of at least one drug substance in said exhaled breath; and wherein said drug substance is selected from the list comprising Amphetamine, ecstasy, Cannabis, THC and cannabinoids, Opiates, heroin, morphine, 6-AM, Cocaine, Benzodiazepines, Propoxyphene, Methadone, Buprenorphine, Tramadol, LSD, Designer/Internet drugs, Kathinon, GHB, Meprobamat, Z-drugs, Tryptamines, Anabolic steroids, or combinations thereof.

7. The method according to claim 1, wherein said aerosols comprise nonvolatile compounds of at least one biomarker in said exhaled breath and wherein said biomarker is selected from the list comprising lipids, peptides, nucleotides, prostanoids, proteins, DNA, RNA, or combinations thereof.

8. The method according to claim 1, further comprising contacting said collected eluate with a SERS surface.

9. The method according to claim 1, further comprising evaporating said solvent from said eluate.

10. The method according to claim 1, further comprising performing a qualitative and/or quantitative analysis of a content comprising said non-volatile compounds on the SERS-surface using SERS-technique.

11. The method according to claim 1, further comprising analyzing said eluate using a mass spectroscopy method.

12. The method according to claim 1, wherein said solvent is methanol.

13. The method according to claim 1, wherein said solvent is acetonitrile.

14. The method of claim 1, further comprising evaporating said eluate at least partially.

15. The method of claim 14, further comprising evaporating said eluate to dryness to form a dry residue to be resuspended in a solvent before being analyzed.

16. A method for recovery of non-volatile compounds from an electrostatic filter membrane, comprising:
providing said electrostatic filter membrane containing an exhaled aerosol comprising a nonvolatile compound, wherein said electrostatic filter membrane is fitted in a housing comprising at least one inlet and at least one outlet;
washing said electrostatic filter membrane with a polar organic solvent while fitted in said housing to form an eluate, the washing including passing the solvent though the housing from one of the inlet or outlet to the other of the inlet or outlet; and
collecting said eluate comprising said nonvolatile compound from the other of said inlet or outlet.

17. The method of claim 16, further comprising analyzing said eluate using an analyzing method, wherein the analyzing method is qualitative or quantitative.

18. A method for recovery of non-volatile compounds from an electrostatic filter membrane, comprising:
providing said electrostatic filter membrane containing an exhaled aerosol comprising a nonvolatile compound;
washing said electrostatic filter membrane with a polar organic solvent to form an eluate;
collecting said eluate comprising said nonvolatile compound; wherein said electrostatic filter membrane is fitted in a housing comprising at least one inlet and at least one outlet, and said washing includes pouring said solvent in one of said inlet or outlet and collecting said eluate through the other; and
evaporating said eluate at least partially.

\* \* \* \* \*